United States Patent [19]

Hirsbrunner et al.

[11] 3,960,942

[45] June 1, 1976

[54] LEUCINE ISOLEUCINE SEPARATION

[75] Inventors: Pierre Hirsbrunner, Corseaux; Raymond Bertholet, Aigle, both of Switzerland

[73] Assignee: Societe D'Assistance Technique pour Produits, Lausanne, Switzerland

[22] Filed: Jan. 20, 1975

[21] Appl. No.: 542,572

[30] Foreign Application Priority Data

Jan. 21, 1974 Switzerland............................ 745/74

[52] U.S. Cl. ........................ 260/534 R; 260/438.1; 260/439 R
[51] Int. Cl.² ........................................... C07C 99/12
[58] Field of Search ................................ 260/534 R

[56] References Cited

UNITED STATES PATENTS

| | | | |
|---|---|---|---|
| 2,471,053 | 5/1949 | Almquist et al. | 260/534 R |
| 2,523,744 | 9/1950 | Warner et al. | 260/534 R |
| 3,084,189 | 4/1963 | Chang | 260/534 G |
| 3,381,031 | 4/1968 | Dwyer et al. | 260/534 R |

Primary Examiner—Joseph E. Evans
Attorney, Agent, or Firm—Kenyon & Kenyon Reilly Carr & Chapin

[57] ABSTRACT

A process for separating leucine and isoleucine from an aqueous solution of these two amino acids, which comprises subjecting their copper or nickel salts to fractional crystallization at, alternately, relatively low and relatively high pH-values in the acid range.

7 Claims, No Drawings

LEUCINE ISOLEUCINE SEPARATION

This invention relates to a process for separating leucine and isoleucine from an aqueous solution of these two amino acids.

Efforts to analyse the exact dietetic requirements of man have opened the way to techniques of preparing foods which inter alia contain so-called essential amino acids in exact proportions. Typical example of a particular food produced by these techniques are the solutions rich in amino acids which are intended for parenteral injection and which are used in place of solutions rich in glucides only. In order to be able to produce a food or to be able to adjust the content in it of one or other component, the components have to be separately available. In particular, essential amino acids have to be available in relatively pure form. Although, in this connection, it may be easy to isolate from a protein a fraction containing leucine and isoleucine alone, there is no easy way of separating isoleucine from that fraction.

One conventional process for separating leucine from isoleucine is based on the fact that one of the two complexes which they form with a copper salt lending itself to complex formation has zero solubility, whilst the other shows low solubility in methanol. It is thus possible to isolate a pure, natural isoleucine by a series of successive crystallisation and extraction operations. The number of repetitions of these operations is high and the yield very low. The same applies to all known processes of this kind. Although significant quantities of isoleucine can be obtained by chemical synthesis, the process is made expensive by the need for subsequent separation of the L- and D-isomers.

The present invention arose out of the need to perfect an industrial process for separating leucine from isoleucine which comprises a small number of operations and involves the use of conventional, inexpensive reactants.

The present invention provides a process for separating leucine and isoleucine from an aqueous solution of these two amino acids which comprises subjecting their copper or nickel salts to fractional crystallisation at, alternately, relatively low and relatively high pH-values in the acid range.

It is desirable for the leucine and isoleucine to be present in the starting solution in a ratio by weight of at most 7:1, because separation becomes very difficult where the ratio is higher, even with the process according to the invention.

The bases and acids which may be used for pH-adjustment may be selected from those which do not form complexes with the metal ion used according to the invention to form the leucinate or isoleucinate.

Preferably, copper sulphate or nickel sulphate is added to the starting solution and the pH-adjustments made by adding sulphuric acid or sodium hydroxide.

Fractional crystallization may be carried out in two successive cycles of two crystallisations each for a starting solution in which the leucine and isoleucine are present in a ratio by weight of greater than 1:1.

pH-Values recommended for the so-called lower crystallisation pH-values are in the range from 2 to 3.8.

It has been found that it is possible in this way to obtain an effective separation quickly and in a highly economic manner. The yield may reach values of significant commercial interest.

The simplicity of the operations and their reduced number are clearly illustrated by the fact that such a yield and such a degree of purity may be obtained with advantage by adjusting the pH-value of an aqueous solution of leucine, isoleucine and copper sulphate to between pH 1.0 and pH 1.8 to form a first, clear solution which is blue in colour, adjusting the pH-value of this first, blue solution to between pH 2 and pH 3, collecting by filtration a first crystallised fraction consisting of copper leucinate, neutralising the filtrate and collecting by filtration a second crystallised fraction consisting of copper leucinate and isoleucinate, dispersing the second crystallised fraction in water, adjusting the pH-value of the resulting dispersion to between pH 1.3 and pH 2.2 and forming a second clear solution which is blue in colour, adjusting the pH-value of the second, blue solution to between pH 2.7 and pH 3.8, collecting by filtration a third crystallised fraction consisting mostly of copper leucinate, neutralising the filtrate and collecting by filtration a fourth fraction consisting mostly of copper isoleucinate.

Once actual separation has been obtained, all that remains is to free the amino acid molecules from the metal ions attached to them, which may be obtained by a high-temperature alkaline treatment for example.

It should be noted that, whenever reference is made here, for reasons of simplicity, to salts of leucine or isoleucine, leucinate or isoleucinate, are meant the complexes formed by the molecules of the amino acid in question with the metal ions in question. In symbolic language, these complexes are reproduced by such expressions as $Cu(Leu)_2$ or $Cu(Ileu)_2$.

It has been found that, although the $Cu^{++}$ ions are particularly suitable for use in the process according to the invention, the $Ni^+$ ions may also be used. It is clear that the number of metal ions to be introduced into the starting solution is proportional to the number of amino acid molecules which it contains.

It should also be noted that the original material of the starting solution to be treated by the process according to the invention may be any source of proteins rich in leucine and isoleucine, such as oil cakes, grains of wheat or maize, microorganisms, especially yeasts, or casein for example. Separation of the proteins from the original material followed by the isolation from those proteins of a fraction containing the crude leucine, namely leucine mixed with isoleucine, may be carried out by any of the methods known among experts.

The invention is illustrated by the following Examples.

EXAMPLE 1

96 g of $CuSO_4.5H_2O$ are added to a solution of 80 g of leucine and 20 g of isoleucine in 1000 g of water. The pH-value is adjusted to 1.5 with 50% sulphuric acid. 30% sodium hydroxide is added to the first, clear blue-coloured solution thus obtained to adjust its pH-value to 2.5. 87 g of crystallised $Cu(Leu)_2$ are retained by filtering on an ordinary paper filter and collected. The pH-value of the filtrate is adjusted to pH 7 by the addition of 30% NaOH. 33 g of a mixture of 50% of $Cu(Leu)_2$ and 50% of $Cu(Ileu)_2$ are retained by filtering on an ordinary paper filter. 20 g of water and 50% sulphuric acid are added to this mixture to obtain a second, clear blue-coloured solution with a pH-value of 1.5. 30% sodium hydroxide is added to this second blue solution to adjust its pH-value to pH 3. 19 g of a mixture of 80% of Cu(Leu)$_2$ and 20% of Cu(Ileu)$_2$ are retained by filtering on an ordinary paper filter and collected. The pH-value of the filtrate is adjusted to pH 7 by the addition of 30% NaOH. 12 g of a mixture of 15% of Cu(Leu)$_2$ and 85% of Cu(Ileu)$_2$, namely copper isoleucinate with a degree of purity of 85%, are collected by filtration on an ordinary paper filter.

The 87 g of Cu(Leu)$_2$ and the 12 g of Cu(Ileu)$_2$ are separately subjected to an identical treatment for separating the copper which is carried out as follows: 300 parts of Cu(Leu)$_2$ or Cu(Ileu)$_2$ mixed with 400 parts of 25% NaOH are held for 1 hour at 85°C. After stirring, the copper oxide is separated by filtration. The filtrate is neutralised with concentrated hydrochloric acid. The amino acids are collected by filtration, washed and dried.

In view of the fact that the 19 g of mixture of 80% of Cu(Leu)$_2$ and 20% of Cu(Ileu)$_2$ may be reused in a starting solution, i.e. recycled, the total yield of leucines is 95%, the losses totalling 5%. The yield of leucine is 98% and the yield of isoleucine 78%.

EXAMPLE 2

After an acid protein hydrolysate has been neutralised and filtered, the residue obtained is dissolved in an acid. The solution is bleached with active carbon and concentrated. The crystallising material is separated, the crude or commercial-grade leucine being obtained in hydrochloride form.

1000 parts (p) of commercial-grade leucine hydrochloride (comm. Leu-HCl), in the present case 120 kg containing 450 p of leucine, 81 p of isoleucine, 23 p of methionine and 34 p of other amino acids, are diluted, heated after the addition of hydrogen peroxide to solubilise the methionine, cooled and filtered at pH 0.5, 280 p of crystallised leucine hydrochloride being collected. 200 p of crystals of which 97.5% consists of leucine and 2.5% of isoleucine, are recovered from these 280 p following dispersion in water, neutralisation with soda and filtration. After adjustment to pH 6 and filtration, the above filtrate obtained by filtration at pH 0.5 yields approximately 300 p of amino acid crystals. After concentration and filtration, the residual solution, to which are added the mother liquors from the above treatment of the 280 p of leucine hydrochloride, yields, on the one hand, mother liquors saturated with sodium chloride, which are eliminated, and on the other hand approximately 100 p of amino acid crystals. Addition of the above 300 p of amino acids to this 100 p gives 400 p of amino acid crystals in which the leucine and isoleucine are present in a ratio by weight of approximately 3.5:1.

375 p of CuSO$_4$.5H$_2$O, 1000 p of water and 150 p of sulphuric acid are added to these 400 p of amino acid crystals to obtain a first, clear blue-coloured solution with a pH-value of 1.2. The pH-value of this solution is adjusted to pH 2.5 by the addition of 30% sodium hydroxide, and 300 p of 97.5% pure Cu(Leu)$_2$ are collected by filtration on an ordinary paper filter. The pH-value of the filtrate is adjusted to pH 7 by the addition of 30% NaOH. 120 p of aino acid crystals are collected by filtration on ordinary filter paper. 200 p of water and 55 p of sulphuric acid are added to these 120 p to obtain a second clear blue-coloured solution with a pH-value of 2. The pH-value of this second, blue solution is adjusted to pH 3.5 and 70 p of a mixture of 70% of Cu(Leu)$_2$ and 30% of Cu(Ileu)$_2$ are collected by filtration. The pH-value of the filtrate is adjusted to pH 7 by the addition of 30% NaOH. 50 p of a mixture of 70% of Cu(Ileu)$_2$, 15% of Cu(Leu)$_2$, 10% of Cu(Val)$_2$ and 5% of complexes of other amino acids with the copper, i.e. 50 p of copper isoleucinate with a degree of purity of 70%, are collected by filtration.

The 300 p of Cu(Leu)$_2$ and the 50 p of Cu(Ileu)$_2$ are subjected to the same treatment as in Example 1 to separate the copper.

In view of the fact that the 70 p of mixture of 70% of Cu(Leu)$_2$ and 30% of Cu(Ileu)$_2$ may be recycled, the yield of leucine (purity 97.5%) is 95%, whilst the yield of isoleucine (purity 70%) is 60%.

What is claimed is:

1. A process for separating leucine and isoleucine from an aqueous solution of these two amino acids, which comprises subjecting their copper or nickel salts to fractional crystallisation at, alternately, relatively low and relatively high pH-values in the acid range and thereafter freeing the amino acids from the salts obtained.

2. A process as claimed in claim 1, wherein the leucine and isoleucine are present in the starting solution in a ratio by weight of at most 7 : 1.

3. A process as claimed in claim 1, wherein copper sulphate or nickel sulphate is added to a starting solution of the two amino acids and the pH-adjustments are made by adding sulphuric acid or sodium hydroxide.

4. A process as claimed in claim 1, wherein fractional crystallisation is carried out in two successive cycles of two crystallisations each for a starting solution in which the leucine and isoleucine are present in a ratio by weight of greater than 1 : 1.

5. A process as claimed in claim 1, wherein the crystallisation at the lower pH value takes place at a pH in the range from 2 to 3.8.

6. A process as claimed in claim 1, wherein the pH-value of a solution of leucine, isoleucine and copper sulphate is adjusted to between pH 1.0 and pH 1.8 and a first, clear blue-coloured solution is obtained, the pH-value of this first blue solution is adjusted to between pH 2 and pH 3, a first crystallised fraction consisting of copper leucinate is collected by filtration, the filtrate is neutralised and a second crystallised fraction consisting of copper leucinate and isoleucinate is collected by filtration, the second crystallised fraction is dispersed in water, the pH-value of the dispersion is adjusted to between pH 1.3 and pH 2.2 and a second, clear blue-coloured solution is obtained, the pH-value of this second, blue solution is adjusted to between pH 2.7 and pH 3.8, a third crystallised fraction consisting mostly of copper leucinate is collected by filtration, the filtrate is neutralised and a fourth crystallised fraction consisting mostly of copper isoleucinate is collected by filtration.

7. A process for separating leucine and isoleucine from an aqueous solution thereof, said process comprising the steps of adding a metal salt selected from the group consisting of copper salts and nickel salts to an aqueous solution containing leucine and isoleucine to form a resultant solution having a pH-value of between 1.0 and 1.8;

thereafter adjusting the pH-value of the resultant solution to a value from 2 to 3.8;

fractionating the resultant solution into a first crystallized fraction consisting of a metal leucinate and a first filtrate;

neutralizing the first filtrate;

obtaining a second crystallized fraction consisting of metal leucinate and isoleucinate from the first filtrate;

forming a second aqueous solution of the second crystallized fraction with a pH-value of between 1.3 and 2.2;

thereafter adjusting the pH-value of the second aqueous solution to a pH-value of from 2.7 to 3.8;

fractionating the resultant second solution into a third crystallized fraction consisting mostly of metal leucinate and to a lesser amount of metal isoleucinate and a second filtrate;

neutralizing the second filtrate;

thereafter collecting a fourth crystallized fraction consisting mostly of metal isoleucinate and to a lesser amount of metal leucinate from the second filtrate; and separating the metal ions from each of the first and fourth fractions to obtain leucine and isoleucine respectively.

* * * * *